(12) United States Patent
Borg et al.

(10) Patent No.: US 10,238,475 B1
(45) Date of Patent: Mar. 26, 2019

(54) ORTHODONTIC FLOSSER

(71) Applicants: N. Michelle Borg, Paradise, CA (US);
John O. H. Niswonger, Calabasas, CA (US)

(72) Inventors: N. Michelle Borg, Paradise, CA (US);
John O. H. Niswonger, Calabasas, CA (US)

(*) Notice: Subject to any disclaimer, the term of this patent is extended or adjusted under 35 U.S.C. 154(b) by 578 days.

(21) Appl. No.: 14/803,359

(22) Filed: Jul. 20, 2015

Related U.S. Application Data

(60) Provisional application No. 62/026,032, filed on Jul. 18, 2014.

(51) Int. Cl.
A61C 15/00 (2006.01)
A61C 15/04 (2006.01)

(52) U.S. Cl.
CPC .................. *A61C 15/046* (2013.01)

(58) Field of Classification Search
CPC .................................................... A61C 15/046

USPC .................. 132/323, 324, 325, 326, 327
See application file for complete search history.

(56) References Cited

U.S. PATENT DOCUMENTS 5,678,578 A * 10/1997 Kossak ................ A61C 15/046
132/322
2008/0289648 A1 * 11/2008 Liu ...................... A61C 15/046
132/325

* cited by examiner

*Primary Examiner* — Todd E Manahan
*Assistant Examiner* — Brianne Kalach
(74) *Attorney, Agent, or Firm* — Ronald L. Rohde

(57) ABSTRACT

A flosser is described that includes a take-up spool for winding a plurality of layers of used floss, a shell for forming a chamber around the take-up spool and enclosing the plurality of layers of used floss windings within the chamber, and helical grooves disposed in an inner surface of the shell for preventing jamming of the take-up spool by accumulated floss windings. The flosser further includes a retie assembly having a groove disposed in a fin for trapping floss against a take-up aperture upon alignment of the groove and aperture, and for urging floss into take-up aperture and wrapping the floss around the take-up spool as the fin rotates further.

13 Claims, 17 Drawing Sheets

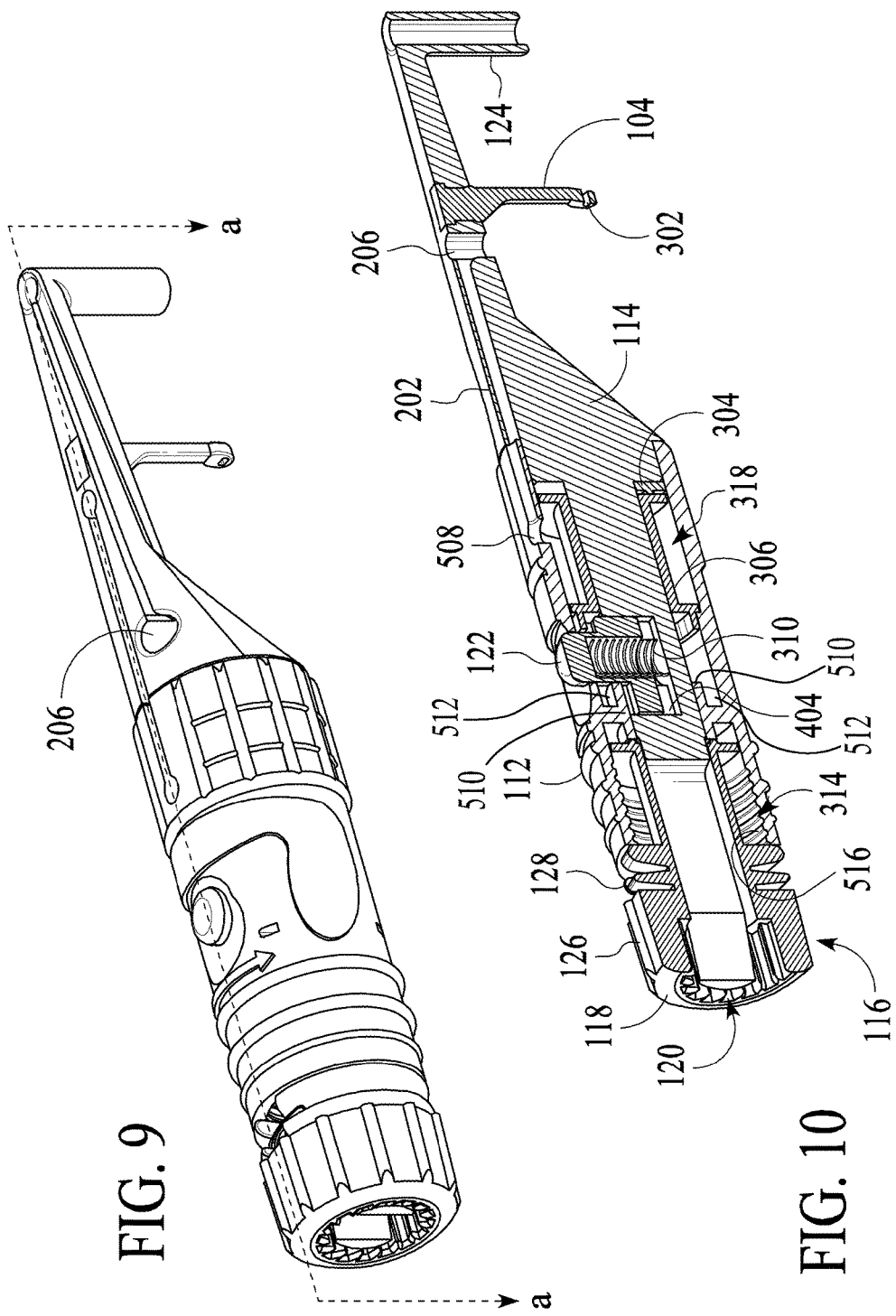

ORTHODONTIC FLOSSER

CROSS-REFERENCE TO RELATED APPLICATIONS

The present application claims priority and benefit of U.S. provisional patent application Ser. No. 62/026,032, filed on Jul. 18, 2014 and titled "ORTHODONTIC FLOSSER," and is related to pending U.S. patent application Ser. No. 14/078,509, filed on Nov. 12, 2013 titled "ORTHODONTIC FLOSSER," and U.S. patent application Ser. No. 13/774,352, filed on Aug. 2, 2011 titled "ORTHODONTIC FLOSSER," (now U.S. Pat. No. 8,967,164, issued Mar. 3, 2015) and to U.S. patent application Ser. No. 13/196,302, filed on Aug. 2, 2011 titled "ORTHODONTIC FLOSSER," (now U.S. Pat. No. 8,671,958, issued Mar. 18, 2014) and to U.S. patent application Ser. No. 12/904,058, filed on Oct. 13, 2010 titled "ORTHODONTIC FLOSSER" (now U.S. Pat. No. 8,387,629, issued Mar. 5, 2013), and to U.S. provisional patent application Ser. No. 61/251,609 filed on Oct. 14, 2009 titled "ORTHODONTIC FLOSSER," and to U.S. provisional patent application Ser. No. 61/241,281, filed on Sep. 10, 2009 and titled "ANTI-MICROBIAL ORTHODONTIC FLOSS." All of the above applications are incorporated by reference herein in their entirety.

BACKGROUND

Field of the Application

The present application relates generally to a flossing apparatus, and more particularly to an orthodontic flosser.

Description of Related Art

Flossing is particularly important for people who have braces. Braces typically include brackets bonded to the surfaces of two or more teeth and a wire or archwire affixed to the brackets. Flossing around braces may be accomplished by threading the floss between the braces and the teeth and then maneuvering a length of the floss into contacts between adjacent teeth. Upon flossing around a pair of teeth and braces, the floss is generally pulled out and then threaded into another position for the next pair of teeth. Unfortunately, threading, inserting, manipulating the floss around the braces, and removing the floss for each pair of teeth can be difficult and time consuming. Maintaining tension on the floss while manipulating the floss between teeth and around braces involves a degree of dexterity and skill that is often beyond the ability of many children and even adults. Frustration due to the difficulty of acquiring skills, manipulating the floss, and the extra time involved in threading and removing the floss can discourage flossing. The purpose of flossing is to remove debris and contamination from contacts between teeth and surfaces around braces to prevent interproximal tooth decay and gum disease. Debris includes particulate matter, dental plaque, and bio films. Contamination includes bacteria and nutrients for the bacteria. Dental plaque tends to adhere to surfaces such as teeth and wires. Floss generally picks up debris and contamination from surfaces of the teeth and the braces in the removal process. Unfortunately, the floss can then redistribute the debris and bacteria to other teeth, interproximal spaces, and braces around the mouth, thus, causing further spreading of tooth decay and gum disease.

BRIEF DESCRIPTION OF THE DRAWINGS

FIG. 9 is a rear perspective view of the body of the flosser of FIG. 1.

FIG. 10 is a side cross section of the flosser of FIG. 9 along line a-a of FIG. 9.

DETAILED DESCRIPTION

Figure 1:
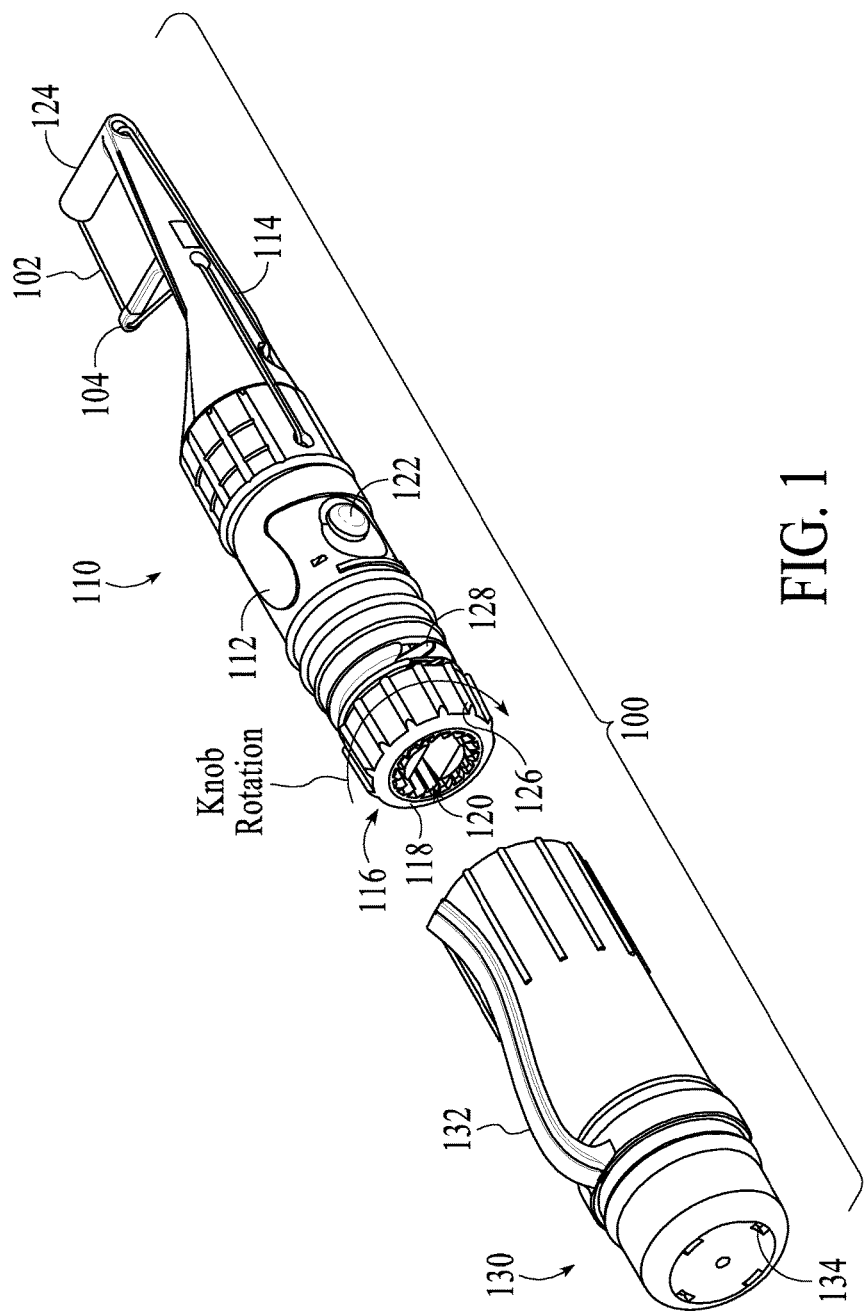
FIG. 1 is a rear perspective view of an embodiment of a flosser, in accordance with aspects of the technology.

FIG. 1 is a rear perspective view of an embodiment of a flosser 100, in accordance with aspects of the technology. The flosser 100 includes a body 110 and a cap 130. The body 110 includes a shell 112, a shaft 114, a take-up assembly 116, a button 122, and floss 102. The shaft 114 includes a head for supporting a flossing prong 104 and a guide 124, which may be used for suspending the floss 102 from the flossing prong 104. The cap 130 includes an optional clip 132, drain holes 134 and internal splines 136 (illustrated in FIG. 12). The take-up assembly 116 includes a knob 118 and a retie assembly 128.

Figure 2:
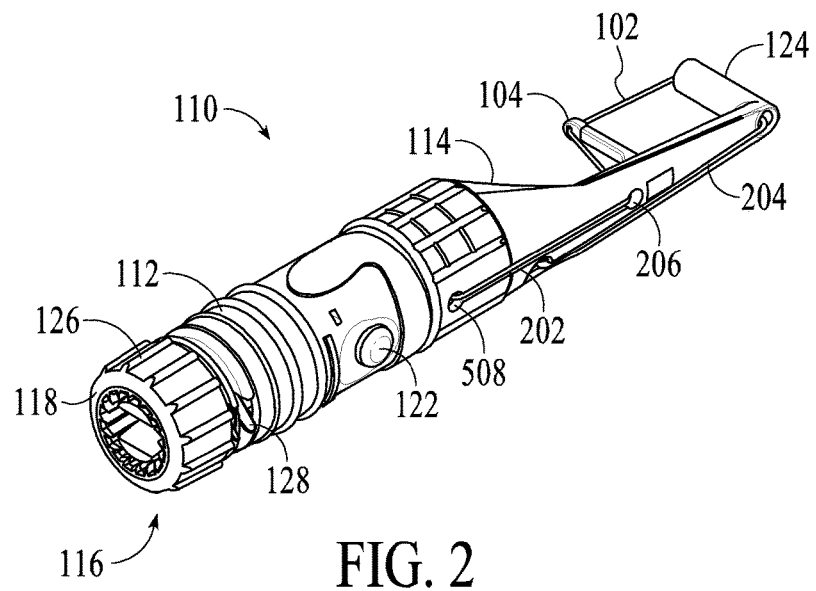
FIG. 2 is a rear perspective view the body of the flosser of FIG. 1 (without the cap).
Figure 3:
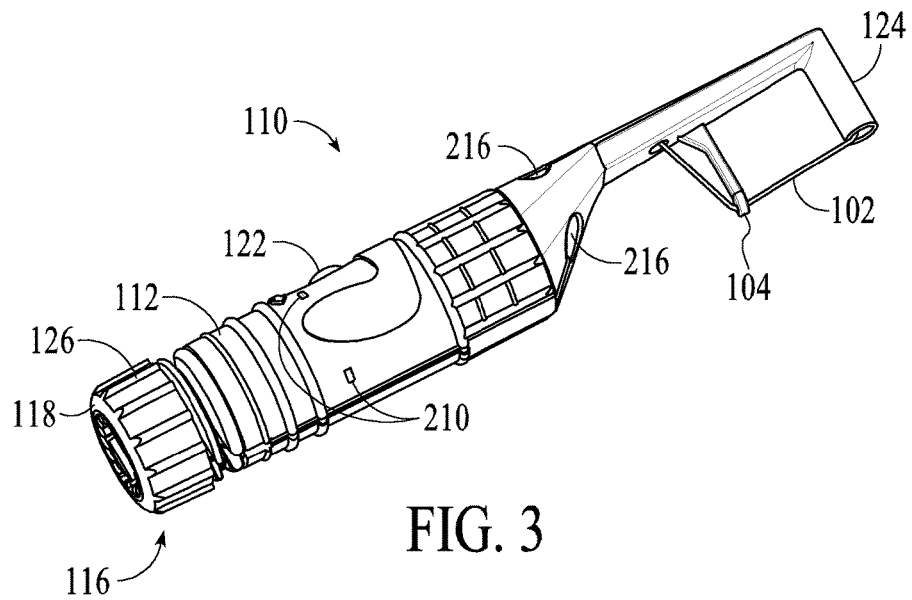
FIG. 3 is a side elevation the body of the flosser of FIG. 1.
Figure 4:
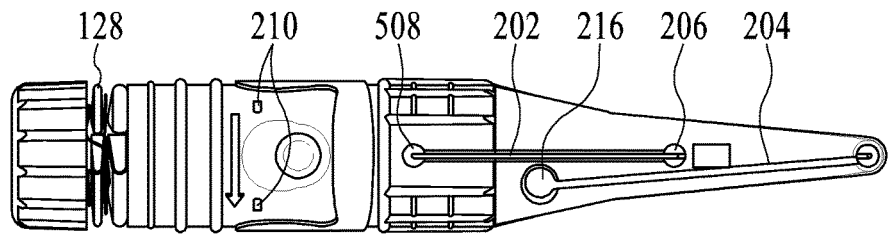
FIG. 4 is a top plan view of the body of the flosser of FIG. 1.
Figure 5:
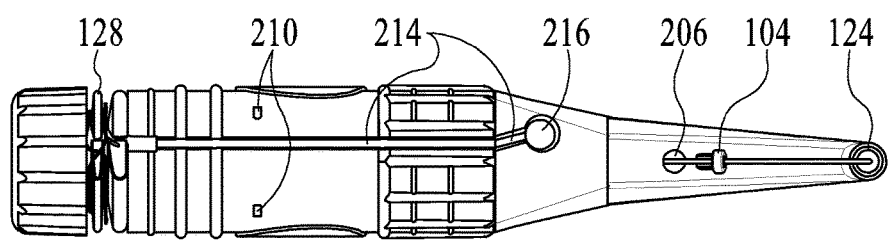
FIG. 5 is a bottom plan view of the body of the flosser of FIG. 1.
Figure 6:
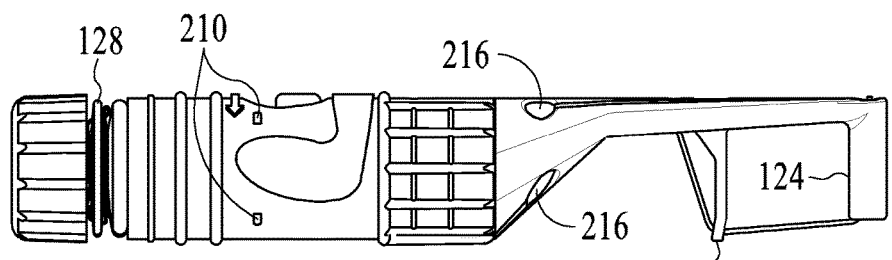
FIG. 6 is a right side elevation of the body of the flosser of FIG. 1.
Figure 7:
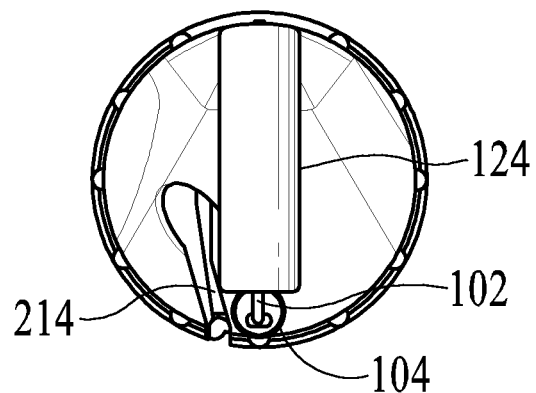
FIG. 7 is an enlarged front elevation of the body of the flosser of FIG. 1.
Figure 8:
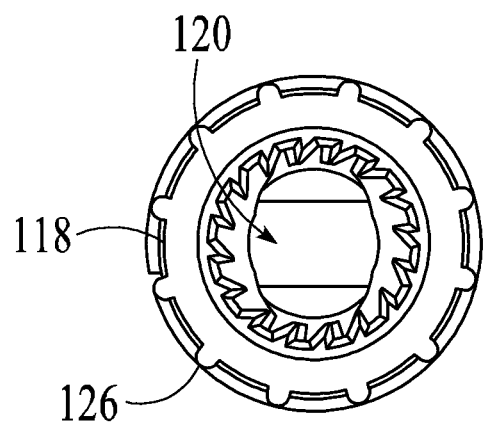
FIG. 8 is an enlarged rear elevation of the body of the flosser of FIG. 1.

FIG. 2 is a rear perspective view the body 110 of the flosser 100 of FIG. 1. FIG. 2 differs from FIG. 1 in that the cap 130 has been omitted. FIG. 3 is a side elevation the body 110 of the flosser 100 of FIG. 1. FIG. 4 is a top plan view of the body 110 of the flosser 100 of FIG. 1. FIG. 5 is a bottom plan view of the body 110 of the flosser 100 of FIG. 1. FIG. 6 is a right side elevation of the body 110 of the flosser 100 of FIG. 1. FIG. 7 is an enlarged front elevation of the body 110 of the flosser 100 of FIG. 1. FIG. 8 is an enlarged rear elevation of the body 110 of the flosser 100 of FIG. 1 The body 110 further includes internal components, including a source spool 306, a spacer clip, and a spring 310, as will be illustrated and discussed elsewhere herein.

Referring to FIGS. 1-8, the shaft 114 may extend through the shell 112 and terminate in a ratchet assembly 120. The shaft 114 may support the source spool 306 (as illustrated elsewhere herein) and engage the take-up assembly 116, securing the take-up assembly 116 to the shell 112. The shaft 114 may also extend forward from the shell 112 to form a head for supporting the prong 104 and the floss guide 124. Floss 102 may be suspended under tension between the prong 104 and floss guide 124.

The ratchet assembly 120 is configured to engage the knob 118 of the take-up assembly 116, which may serve to secure the shaft 114 to the take-up assembly 116 and constrain the shaft 114 within the shell 112. In some embodiments, the knob 118, take-up spool 610 (illustrated elsewhere herein), and retie assembly 128 of the take-up assembly 116, are fabricated from a single piece of material, for example, using injection molding. The knob 118 is configured to be grasped and rotated by a user. The ratchet assembly 120 is configured to bias rotation of the knob 118 in one direction, e.g., in clockwise direction indicated by the knob rotation arrow in FIG. 1. The retie assembly 128 is configured for use in securing a broken end of the floss 102 to the take-up spool 610. A button 122 is configured to release the source spool 306 for rotation to pay out floss 102. Rotation of the knob 118 may be used to advance the floss 102 or apply tension to the floss 102, depending on a position of the button 122. For example, rotation of the knob 118 may be used to advance the floss 102 when the button 122 is pressed, and to apply tension to the floss 102 when the button 122 is released. Referring to FIG. 5, the shell 112 and shaft 114 include a lower used floss groove 214 disposed along the bottom of the shell 112 and shaft 114 for conducting used floss.

An engagement of the ratchet assembly 120 with the take-up assembly 116 may form a ratchet and pawl to bias rotation of take-up assembly 116 using the knob 118 (e.g., in the direction of the arrow in FIG. 1) and prevent or reduce counter rotation of the take-up assembly 116. The knob 118 may include external splines 126 configured to provide a grip for rotating the take-up assembly 116. The external splines 126 may also engaging the cap 130 when rotating the take-up assembly 116. The retie assembly 128 may be used for winding a broken end of floss 102 while retying the broken floss 102. The take-up spool 610 may be used for winding used floss.

FIG. 9 is a rear perspective view of the body 110 of the flosser 100 of FIG. 1. FIG. 10 is a side cross section of the flosser 100 of FIG. 9 along line a-a of FIG. 9. Referring to FIG. 10, the source spool 306 may be disposed on the shaft 114 internal to the shell 112. A spacer clip 304 may be used for positioning a source spool 306 during installation on the shaft 114. The source spool 306 and shell 112 may form a source chamber 318. The button 122 may be disposed in a button guide slot 404 on the shaft 114 and configured to engage the source spool 306, as will be described elsewhere herein. A spring 310 may be configured to hold the button 122 in an engagement position with respect to the source spool 306. The take-up assembly 116 is configured to engage the shaft 114 and may secure the shell 112, button 122, and source spool 306 to the shaft 114. The take-up assembly 116 (illustrated in more detail FIGS. 22-25) includes a take-up spool 610 that forms a take-up chamber 314 within the shell 112. The shell 112 (illustrated in more detail FIGS. 20-21) includes helical grooves 516 within the take-up chamber 314 that are configured to urge used floss forward along the take-up spool 610 and away from the retie assembly 128. The knob 118 and a portion of shaft 114 form a ratchet assembly 120. Ratchet 602 (see FIGS. 22-25) may be disposed around an inner surface of the knob 118 and pawl 408 may be disposed at an end of the shaft 114 (see FIGS. 14-19).

The source spool 306 may feed floss 102 through a spool aperture 504 in the shell 112 for suspension of the floss 102 between the prong 104 and guide 124, as will be described elsewhere herein. The floss may be routed back to the retie assembly 128 and then into the take-up chamber 314 formed by the spool. The floss 102 may be wrapped around the take-up spool 610 as it is used. The floss 102 may be placed under tension using the take-up assembly 116. Routing of the floss will be illustrated further elsewhere herein.

FIG. 10 further illustrates a seal between the shell 112 and the shaft 114 formed by a bearing 510. The bearing 510 may form an interference fit with the shaft 112. A draft angle may be used for the bearing 510 and/or a portion of the shaft within the bearing. The draft angle may serve to simplify installation of the shell 112 on the shaft 114 in view of the interference fit. The seal may isolate the take-up chamber 314 from the source chamber 318. A drain chamber 512 may collect water from the source chamber 318 and allow the water to drain out the drain holes 210.

Figure 11:
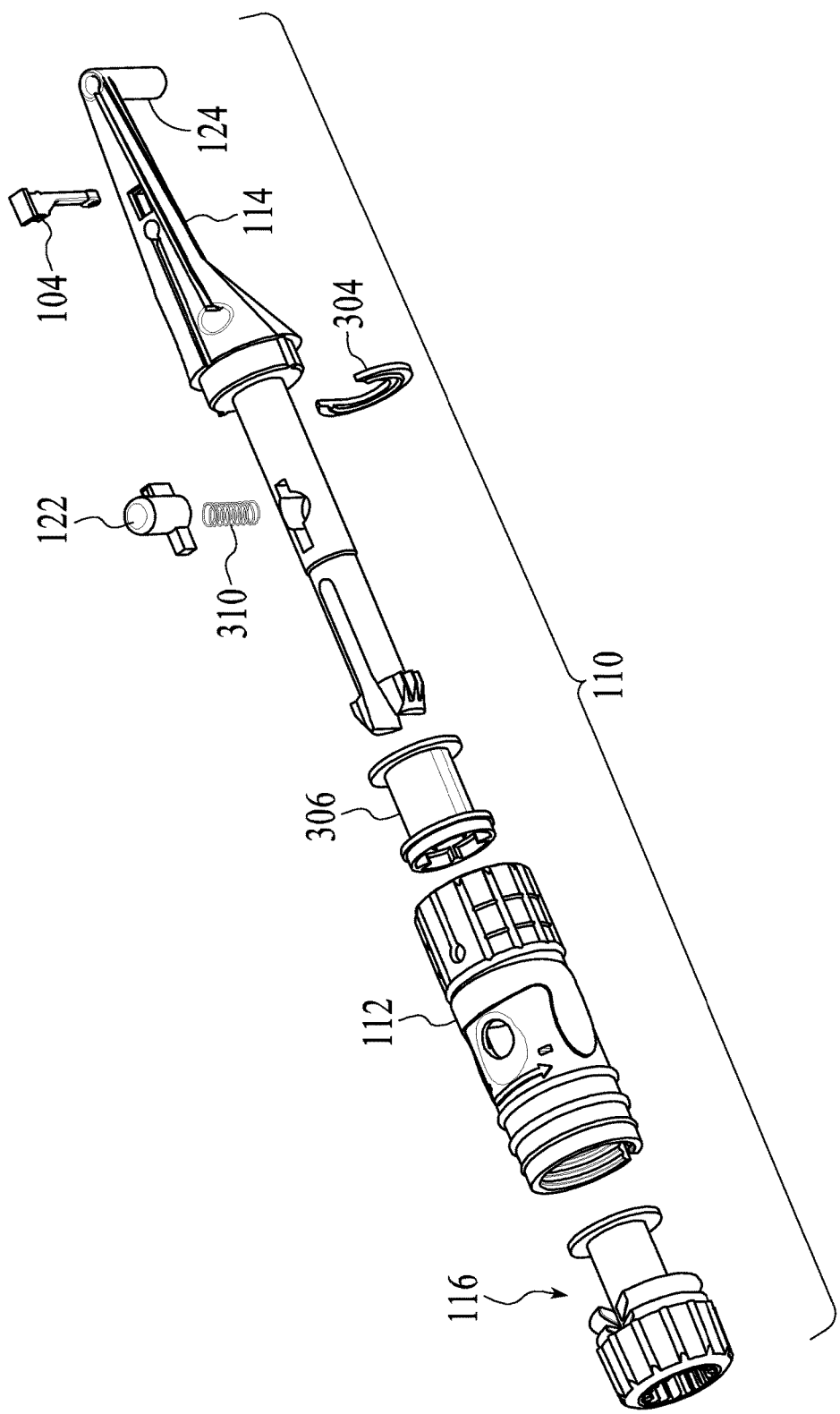
FIG. 11 is an exploded view of the flosser body of FIG. 1.
Figure 12:
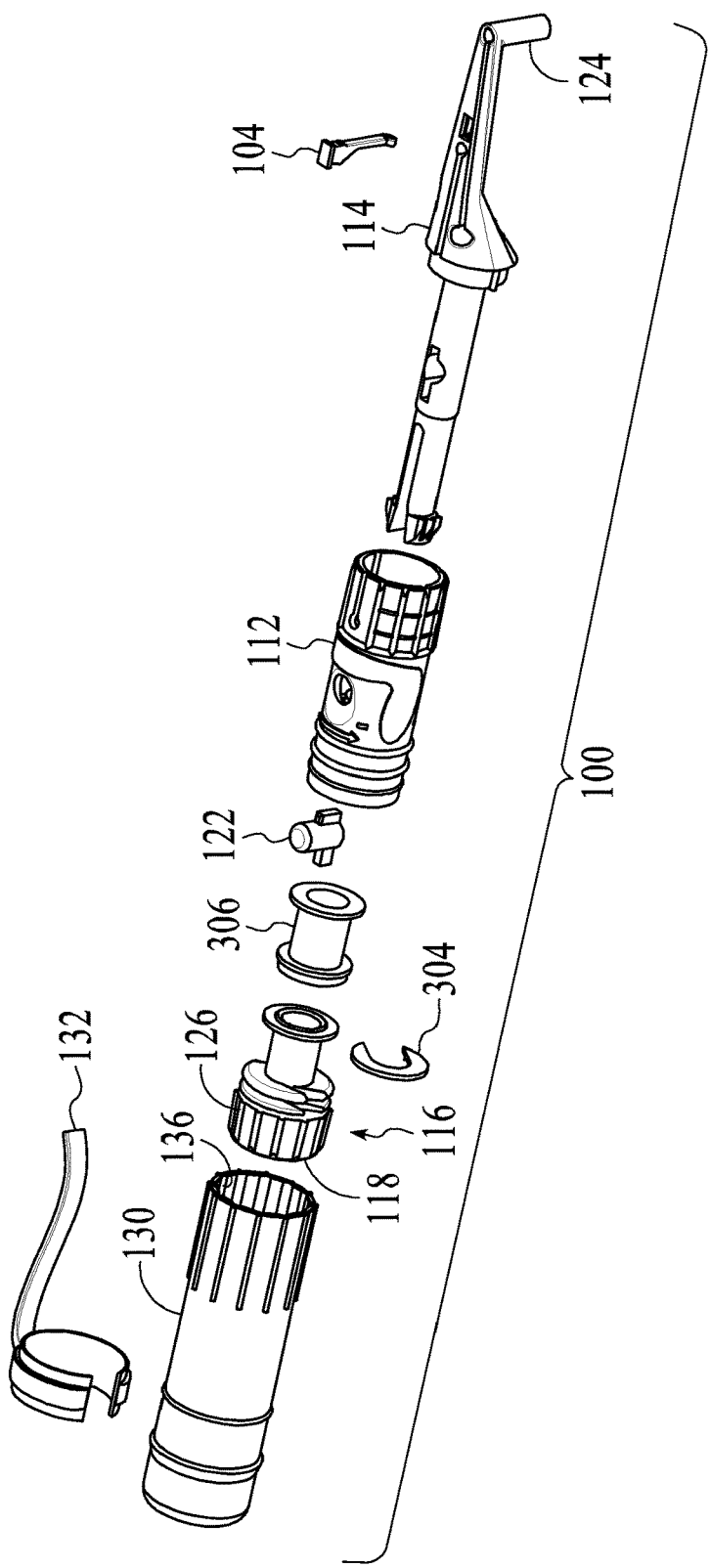
FIG. 12 is an exploded view of the flosser of FIG. 1, including a cap and clip.

FIG. 11 is an exploded view of the flosser body 110 of FIG. 1. FIG. 12 is an exploded view of the flosser 100 of FIG. 1, including the cap 130 and clip 132. The arrangement of the parts in FIG. 12 may not be entirely representative of the arrangement of parts following assembly.

Referring to FIG. 12, the cap 130 may include internal splines 136 configured to engage external splines 126 disposed on an outer surface of the knob 118. The splines 126 and 136 may transmit torque from the cap 130 to the knob 118 for rotating the knob 118 to advance floss through the flosser 100 as described elsewhere herein. The cap 130 is further configured to cover the guide 124 and prong 104, and engage the shell 112 using a detent to protect the floss 102, guide 124, and prong 104 from dirt, debris, and contamination.

Figure 13:
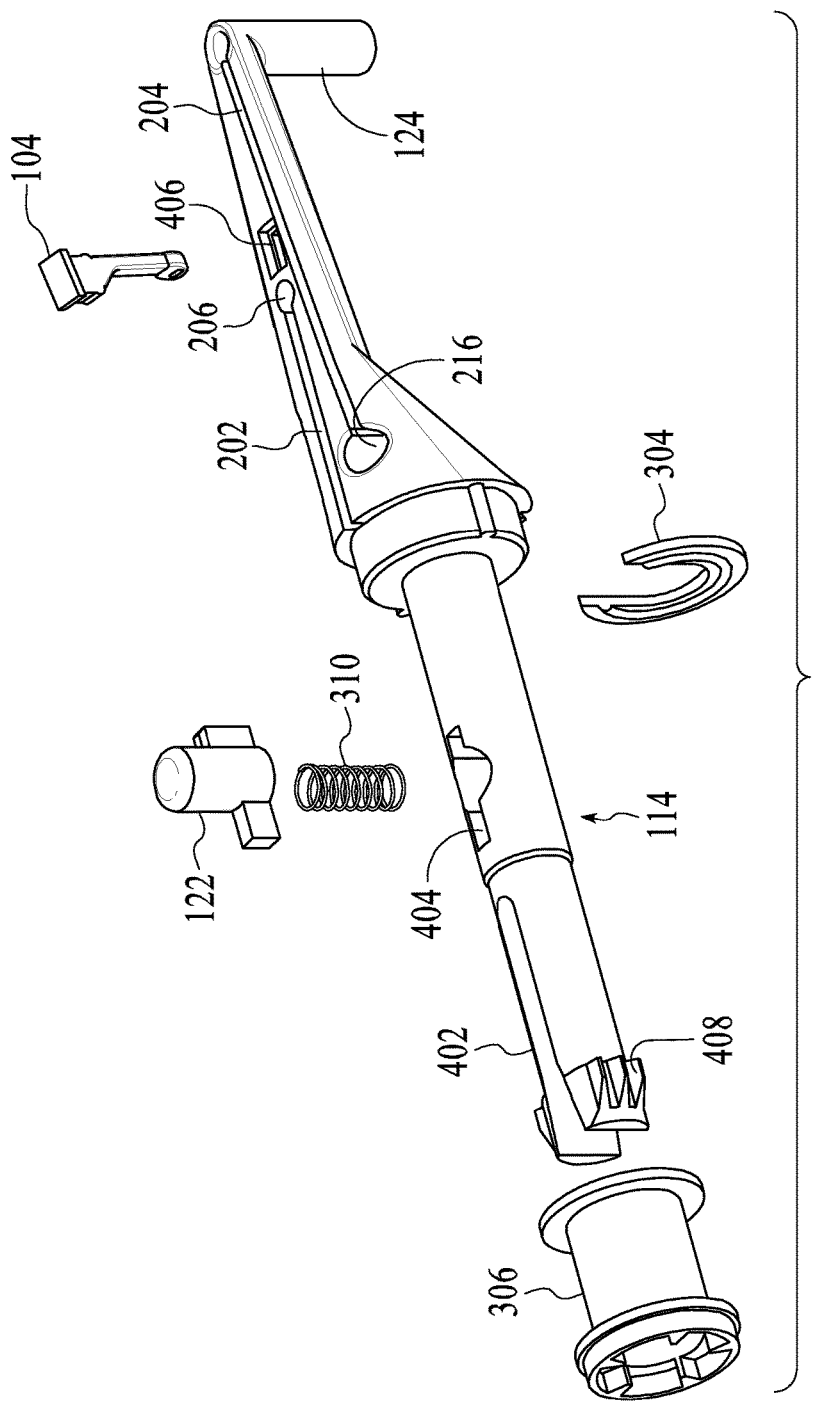
FIG. 13 is an enlarged exploded view of internal components of the flosser body of FIG. 11.

FIG. 13 is an enlarged exploded view of internal components of the flosser body 110 of FIG. 11. FIG. 13 illustrates an arrangement for installing the source spool 306, the spacer 304, the button 122, the spring 310, and the prong 104 on the shaft 114. The source spool 306 may be installed on the shaft 114 followed by the spring 310 and the button 122. The spacer 304 may then be inserted forward of the source spool 306 to slide the source spool 306 backwards over a portion of the button 122. The prong 104 may be installed before or after the source spool 306.

Figure 14:
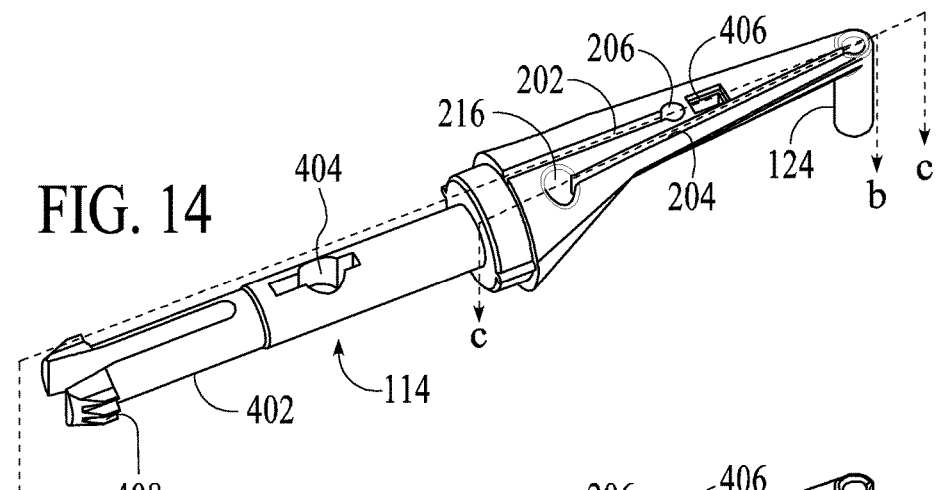
FIG. 14 is a rear perspective view of the shaft of the flosser body of FIG. 1.
Figure 15:
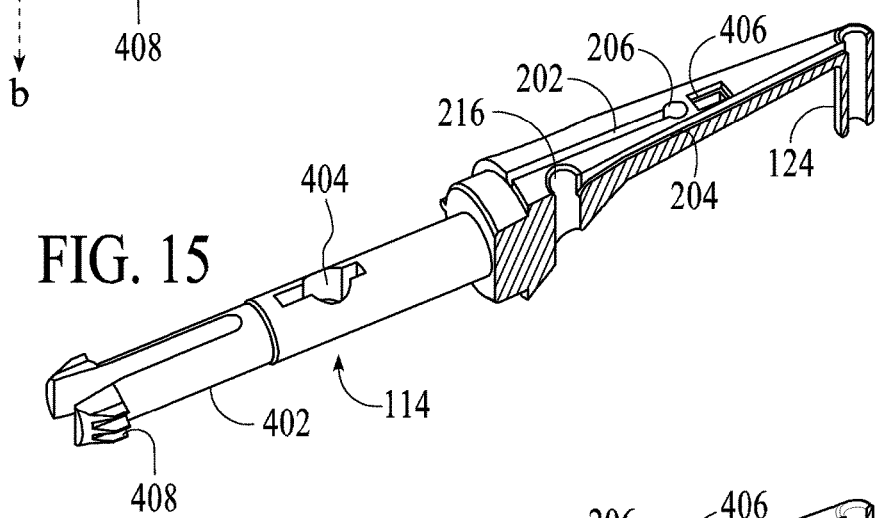
FIG. 15 is perspective view of a partial cut-away of the shaft taken along line c-c of FIG. 14.
Figure 16:
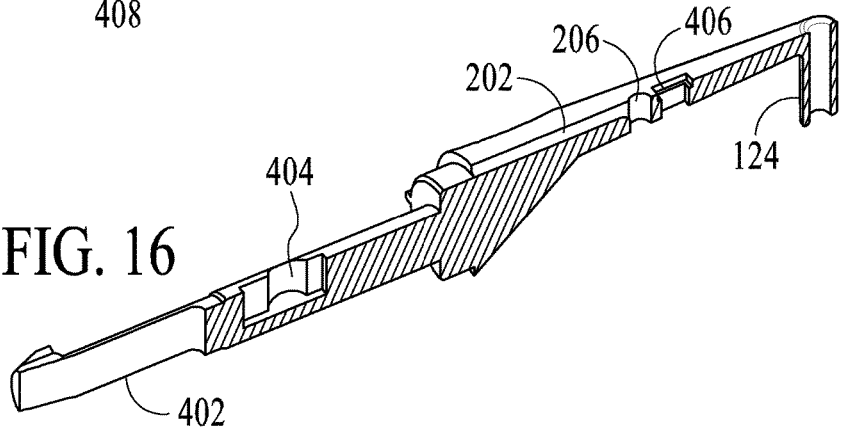
FIG. 16 is a perspective view of a cross section of the shaft taken along line b-b of FIG. 14.
Figure 17:
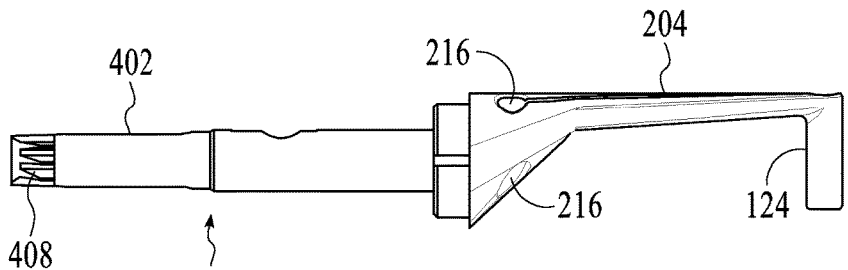
FIG. 17 is a side elevation of the shaft of the flosser body of FIG. 1.
Figure 18:
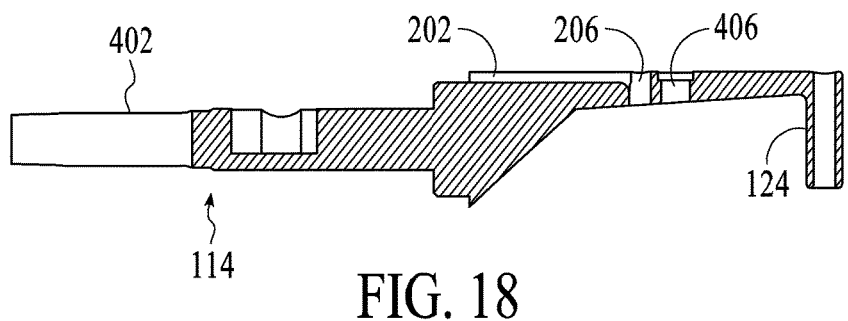
FIG. 18 is a cross section of the shaft taken along line b-b of FIG. 14.
Figure 19:
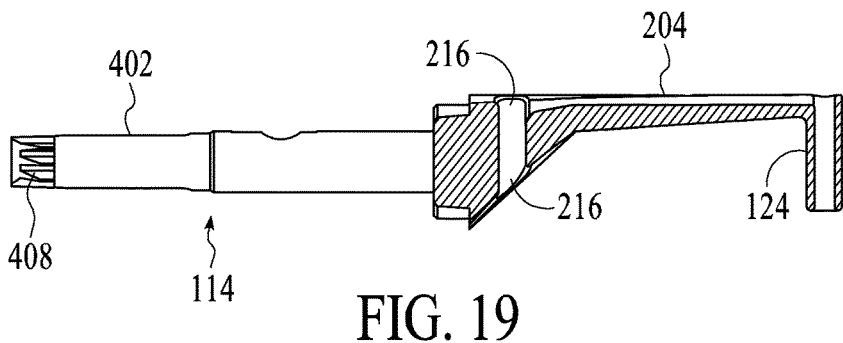
FIG. 19 is cut-away view of the shaft of FIG. 16 taken along line c-c of FIG. 14.

FIGS. 14-19 illustrate details of the shaft 114. FIG. 14 is a rear perspective view of the shaft 114 of the flosser body 110 of FIG. 1. FIG. 15 is perspective view of a partial cut-away of the shaft 114 taken along line c-c. FIG. 16 is a perspective view of a cross section of the shaft 114 taken along line b-b. FIG. 17 is a side elevation of the shaft 114 of the flosser body 110 of FIG. 1. FIG. 18 is a cross section of the shaft 114 taken along line b-b of FIG. 14. FIG. 19 is cut-away view of the shaft 114 of FIG. 16 taken along line c-c of FIG. 14.

The shaft 114 includes a button guide slot 404 configured for accepting the button 122 and providing space for movement of the button 122. The shaft 114 further includes spring forks 402. The spring forks 402 may include pawls 408 disposed on the ends of the spring forks 402. The pawls may have a radius larger than an inner diameter of a portion of take-up assembly 116. The spring forks 402 are configured to deflect inward while installing the take-up assembly 116, and optionally the source spool 306, over the pawls 408. The radius of the pawls 408 being larger than the internal diameter of the knob 118, may hold the take-up assembly 116 to the shaft 114.

The shaft 114 includes a source groove 202 and a source aperture 206. The source groove 202 on the shaft 114 is configured for routing fresh source floss from the source floss groove 506 on the shell 112 (illustrated elsewhere herein) to the source aperture 206. The source aperture 206 is configured for routing floss from the top of the shaft 114 to the prong floss aperture 302 below the shaft 114. In some embodiments, the shaft 114 includes a used floss aperture 216. The shaft 114 may also include an upper used floss groove 204 for routing used floss from the guide 124 to the used floss aperture 216. The used floss aperture 216 is configured for routing used floss from the upper used floss groove 204 on the top of the shaft 114 to the lower used floss groove 214 on the bottom of the shell 112 and shaft 114.

Figure 20:
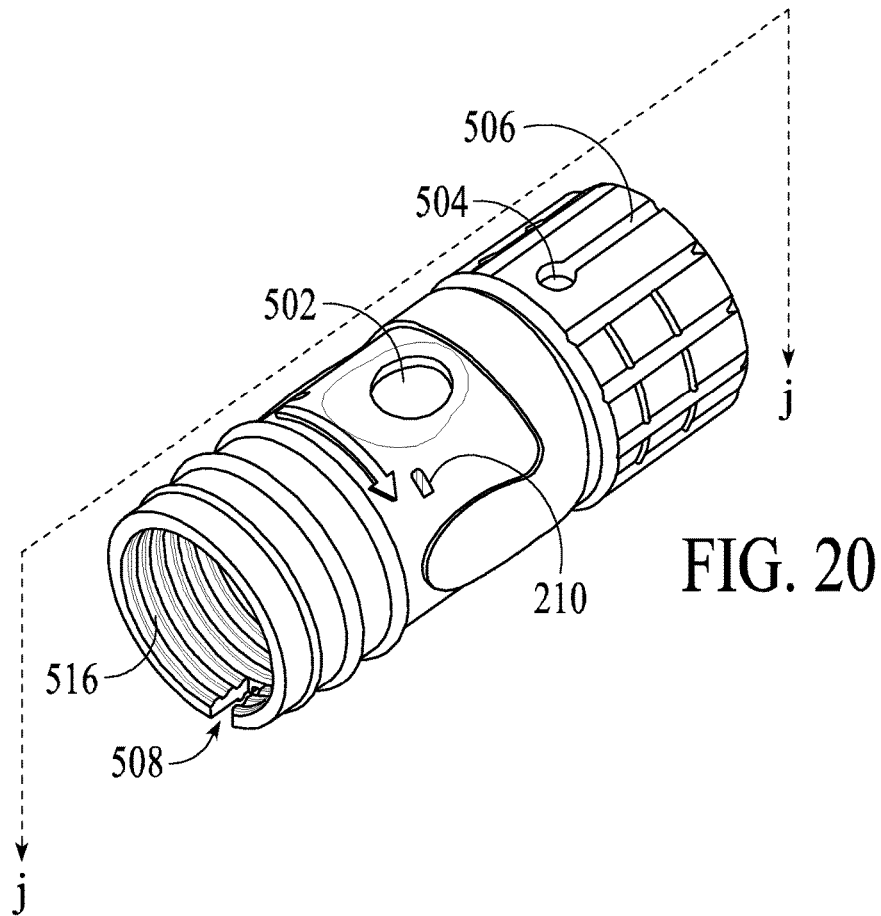
FIG. 20 is a rear perspective view of the shell of the flosser body of FIG. 1.
Figure 21:
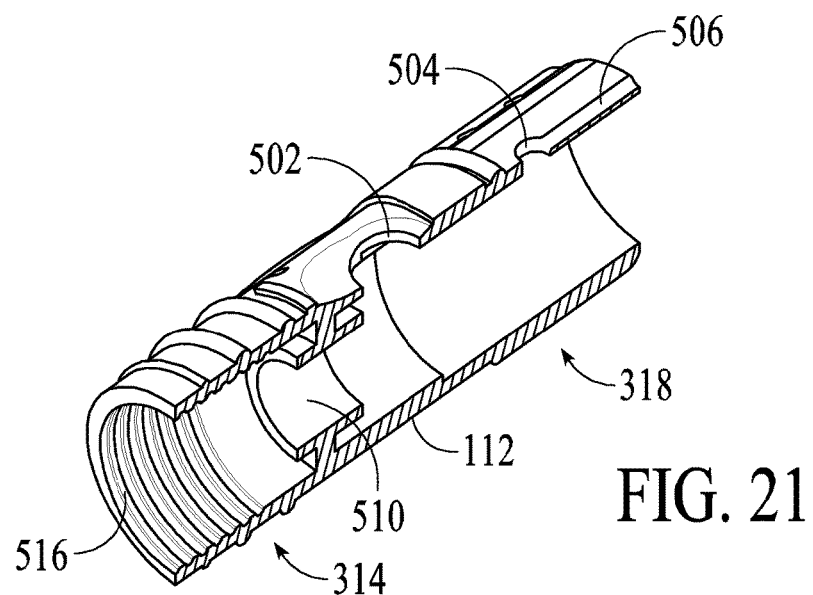
FIG. 21 is a cross section view of the shell along line j-j of FIG. 20.

FIGS. 20 and 21 illustrate details of the shell 112. FIG. 20 is a rear perspective view of the shell 112 of the flosser body 110 of FIG. 1. FIG. 21 is a cross section view of the shell 112 along line j-j of FIG. 20. The shell 112 includes a button aperture 502, a spool aperture 504, a source floss groove 506, a take-up aperture 508, and drain holes 210. The shell 112 also includes a portion of the lower used floss groove 214 illustrated in other figures. The drain holes 210 are configured for allowing water to drain out of the drain chamber 512 in the source chamber 318 after rinsing the flosser 100.

Figure 22:
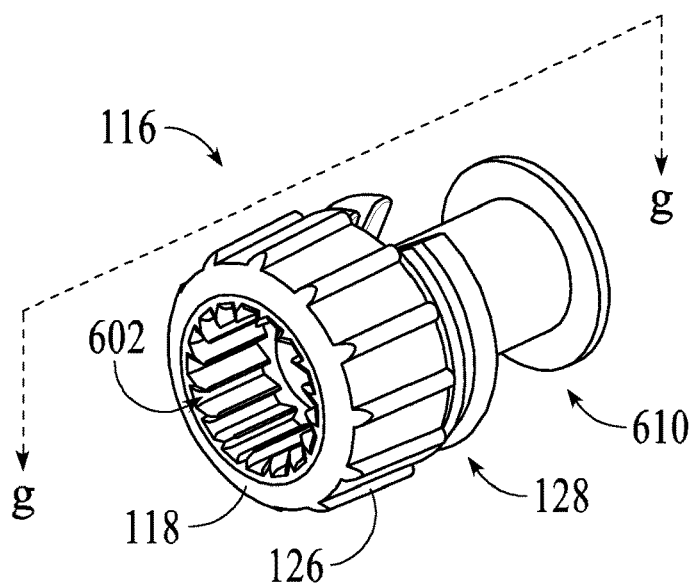
FIG. 22 is a rear perspective view of the take-up assembly of the flosser of FIG. 1.
Figure 23:
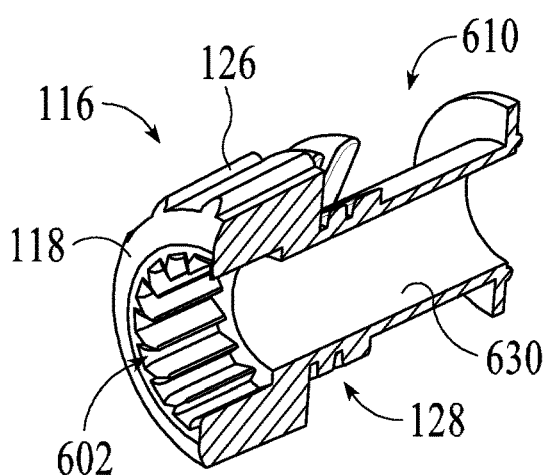
FIG. 23 is a cross section view of the take-up assembly along line g-g of FIG. 22.
Figure 24:
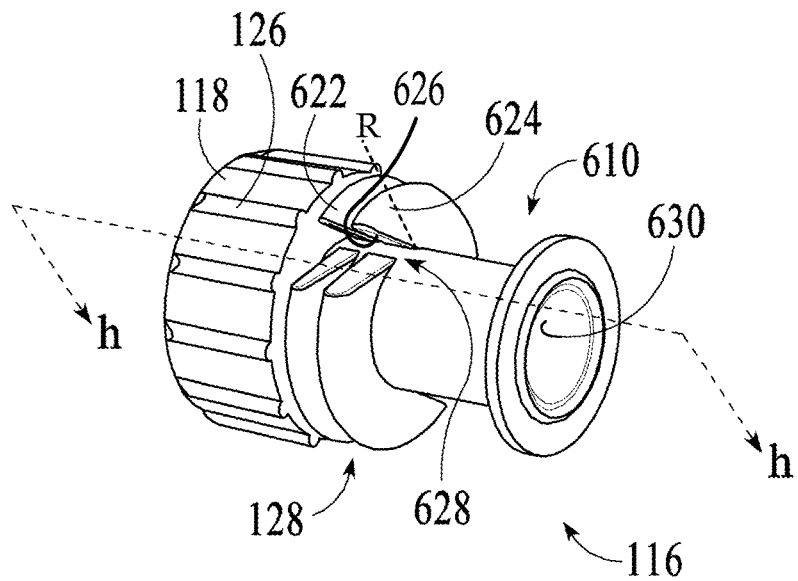
FIG. 24 is a front perspective view of the take-up assembly of the flosser of FIG. 1.
Figure 25:
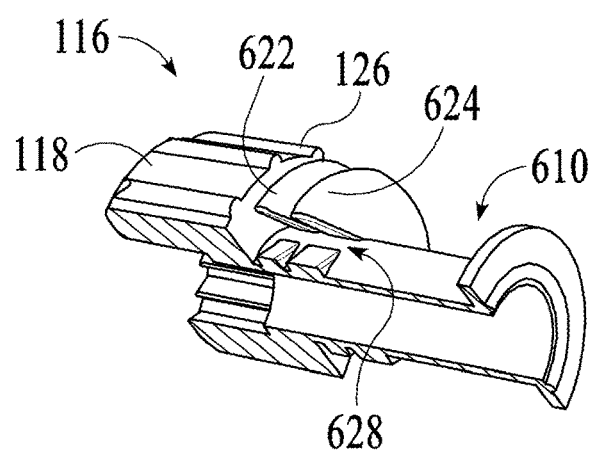
FIG. 25 is a cross section view of the take-up assembly along line h-h of FIG. 24.

FIGS. 22-25 illustrate details of the take-up assembly 116. FIG. 22 is a rear perspective view of the take-up assembly 116 of the flosser 100 of FIG. 1. FIG. 23 is a cross section view of the take-up assembly 116 along line g-g of FIG. 22. FIG. 24 is a front perspective view of the take-up assembly 116 of the flosser 100 of FIG. 1. FIG. 25 is a cross section view of the take-up assembly 116 along line h-h of FIG. 24.

Referring to FIGS. 22-25, the take-up assembly 116 includes a knob 118, a retie assembly 128, and a take-up spool 610. The retie assembly 128 includes a retie fin 624. The retie assembly 128 also includes an optional holding fin 622. A retie groove 628 may be disposed in retie fin 624. The retie groove 628 of FIG. 25 is illustrated as being disposed in both the holding fin 622 and the retie fin 624. However, in some embodiments, a separate groove is disposed in the holding fin 622 that is not aligned with the retie groove 628. Two retie grooves 628 are illustrated as being about 180 degrees apart in FIGS. 22-25. However, the retie assembly 128 may have one retie groove 628, or more than two retie grooves 628. A trailing edge 626 of the retie groove 628 is illustrated as being at an acute angle with respect to a radial direction represented by a dotted radial line R, extending from the axis of the retie assembly 128. The angle may provide for trapping floss between the retie groove and the take-up aperture 508.

The take-up assembly 116 further includes a take-up bearing 630 for rotation of the take-up assembly 116 about the spring forks 402. A plurality of ratchets 602 may be disposed about an inner surface of the knob 118.

Figure 26:
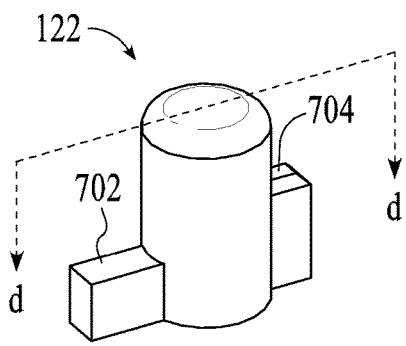
FIG. 26 is a top rear perspective view of the button of the flosser of FIG. 1.
Figure 27:
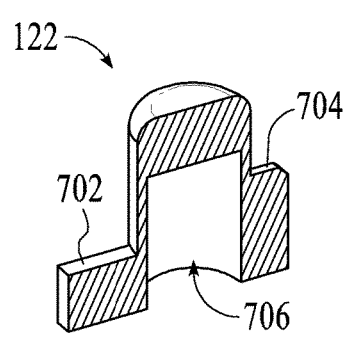
FIG. 27 is a cut-away view of the button of FIG. 26.

FIGS. 26 and 27 illustrate details of the button 122. FIG. 26 is a top rear perspective view of the button 122 of the flosser 100 of FIG. 1. FIG. 27 is a perspective cross section view of the button 122 of FIG. 26 along line d-d of FIG. 26. The button 122 includes a guide fin 702 and a spool stop 704. The guide fin 702 is configured for engaging a button guide slot 404 disposed in the shaft 114 for maintaining orientation of the button 122 while the button 122 is being pressed to release the source spool 306. The spool stop 704 is configured for engaging splines of the source spool 306 when the button 122 is not pressed and releasing the splines of the source spool 306 to permit free rotation of the source spool 306 when the button 122 is pressed.

Figure 28:
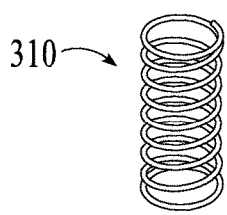
FIG. 28 is a perspective view of the spring of the flosser of FIG. 1.

FIG. 28 is a perspective view of the spring 310 of the flosser 100 of FIG. 1. The spring 310 is configured to hold the button 122 in an engagement position with the splines of the source spool 306. The spring 310 may be sized to fit inside a cavity 706 of the button 122.

Figure 29:
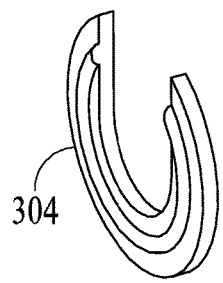
FIG. 29 is a rear perspective view of the spacer clip of the flosser of FIG. 1.
Figure 30:
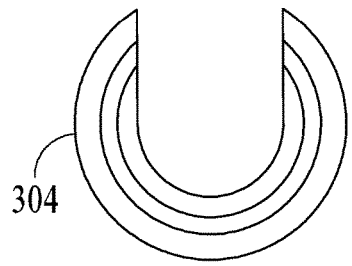
FIG. 30 is a rear elevation of the spacer clip of the flosser of FIG. 1.

FIGS. 29 and 30 illustrate the spacer clip 304. FIG. 29 is a rear perspective view of the spacer clip 304 of the flosser 100 of FIG. 1. FIG. 30 is a rear elevation of the spacer clip 304 of the flosser 100 of FIG. 1. The spacer clip 304 is configured to urge the source spool 306 backwards against the button 122, after installation of the button 122. This may position the source spool 306 in an engagement position with respect to the button 122 such that the spool stop 704 engages the splines of the source spool 306. The shell 112 may hold the spacer clip 304 in position. The button 122 may render the source spool 306 easier to install. Without the spacer clip 304 in place the source spool 306 may slide forward on the shaft 114 during installation of the button. After installation of the button 122, the source spool 306 may be slid into engagement position with respect to the button 122 and the spacer clip 304 installed to hold the button 122 in the engagements position.

Figure 31:
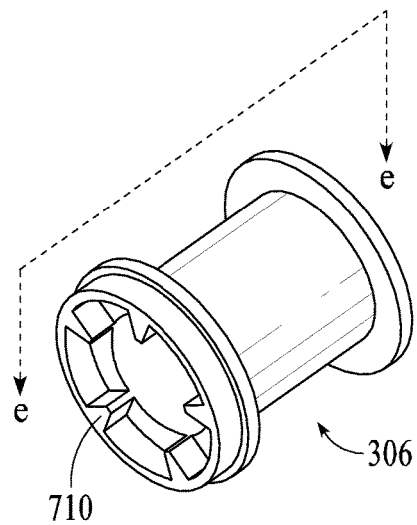
FIG. 31 is top rear perspective view of the source spool of the flosser of FIG. 1.
Figure 32:
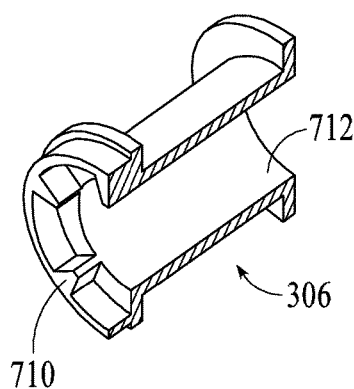
FIG. 32 is a cross section view of the source spool along line e-e of FIG. 31.

FIGS. 31 and 32 illustrate details of the source spool 306. FIG. 31 is top rear perspective view of the source spool 306 of the flosser 100 of FIG. 1. FIG. 32 is a cross section view of the source spool 306 along line e-e of FIG. 31. The source spool 306 includes splines 710 for engaging the spool stop 704 of the button 122. While the splines 710 engage the spool stop 704, the source spool 306 is prevented from rotating, which allow tension to be applied to the floss 102. The source spool 306 is configured to dispense floss 102 from the source chamber 318 for routing through the flosser body 110. As the source spool 306 rotates about the shaft 114 on a source spool 306 bearing, the floss 102 may be advanced through the flosser body 110.

Figure 33:
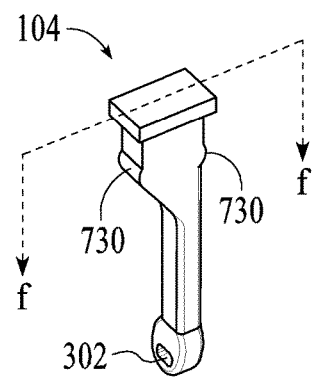
FIG. 33 is a rear perspective view of the prong of the flosser of FIG. 1.
Figure 34:
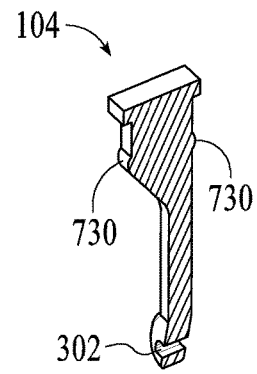
FIG. 34 is a cross section of the prong of FIG. 33 along line f-f of FIG. 33.

FIGS. 33 and 34 illustrate details of the prong 104. FIG. 33 is a rear perspective view of the prong 104 of the flosser 100 of FIG. 1. FIG. 34 is a cross section of the prong 104 of FIG. 33 along line f-f of FIG. 33. The prong 104 includes a prong floss aperture 302. Floss may be threaded through the prong floss aperture 302 for suspension between the prong 104 and the guide 124. The prong 104 also includes detents 730 configured for allowing the prong 104 to be installed in the prong aperture 406 by simply pushing the prong 104 into the prong aperture 406. The detents 730 may hold the prong 104 within the prong aperture 406 after installation.

Figure 35:
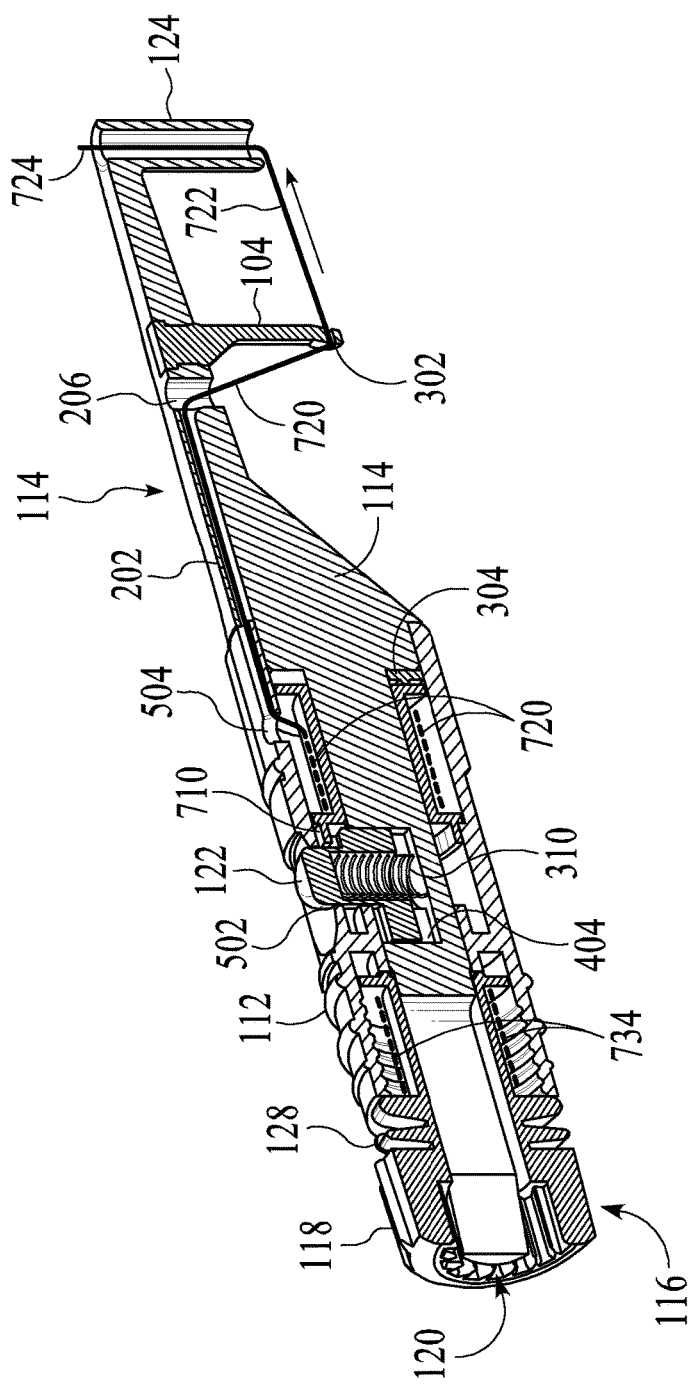
FIG. 35 is a cross section of the flosser body of FIG. 10 illustrating routing of the floss.
Figure 36:
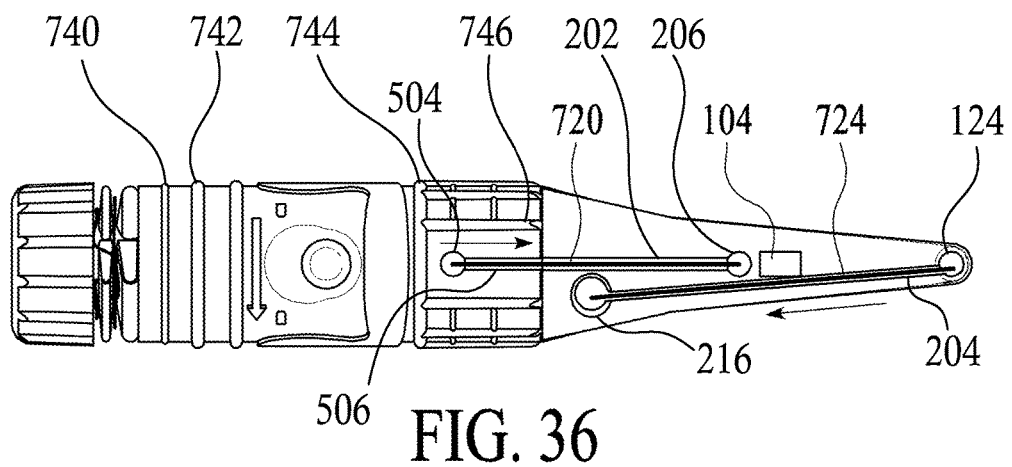
FIG. 36 is a top plan view of the flosser body of FIG. 1 illustrating routing of the floss.
Figure 37:
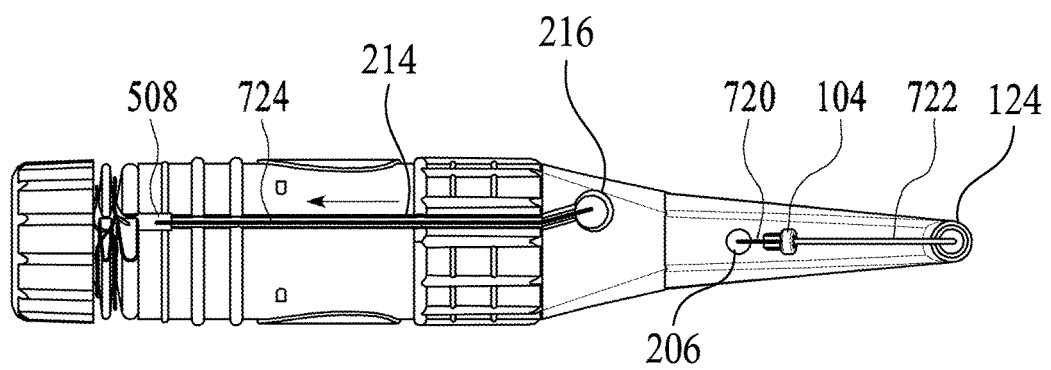
FIG. 37 is a bottom plan view of the flosser body of FIG. 1 illustrating routing of the floss.

FIGS. 35-37 illustrate details of routing floss 102 through the flosser 100. FIG. 35 is the cross section of the flosser body 110 of FIG. 10. FIG. 35 differs from FIG. 10 in that FIG. 35 illustrates routing of the floss 102 through the flosser body 110. FIG. 36 is a top plan view of the flosser body 110 of FIG. 4. FIG. 36 differs from FIG. 4 in that FIG. 36 illustrates routing of the floss 102, including source floss 720, usable floss 722, and used floss 724 through the flosser body 110. FIG. 37 is a bottom plan view of the flosser body 110 of FIG. 5. FIG. 37 differs from FIG. 5 in that FIG. 37 illustrates routing of the floss 102, including source floss 720, usable floss 722, and used floss 724 through the flosser body 110.

The routed portions of the floss 102 include source floss 720 from the source spool 306 to the prong floss aperture 302, usable floss 722 suspended between the prong floss aperture 302 and the guide 124, and used floss 724 between the guide 124 and the take-up spool 610.

Referring to FIGS. 35-36, fresh source floss 720 in the source chamber 318 may be wrapped around the source spool 306 and fed out of the source chamber 318 through the spool aperture 504 in the shell 112. The source floss 720 may traverse the source floss groove 506 in the shell 112 and a source groove 202 in the shaft 114 in the direction indicated by the arrow. These grooves may be disposed between the spool aperture 504 in the shell 112 and the source aperture 206 in the shaft 114. The source floss 720 may be fed down through the source aperture 206 from the top of the shaft 114 to the prong floss aperture 302 below the shaft 114.

Referring to FIGS. 35-37, the usable floss 722 may be suspended between the prong 104 and guide 124 and used for cleaning teeth. The used floss 724 may be routed up through the guide 124 to the top of the shaft 114 and then along the upper used floss groove 204 in the top of the shaft 114 to a used floss aperture 216. At the used floss aperture 216, the used floss 724 may be routed down through the used floss aperture 216 to the lower used floss groove 214 on the bottom of the shaft 114 and the shell 112. The used floss 724 may then be routed along the used floss groove 214 in the shell 112 to the take-up aperture 508 adjacent the retie assembly 128. The used floss 724 may be routed through the take-up aperture 508 into the take-up chamber 314 formed by the take-up spool 610 and the shell 112, and wrapped around the take-up spool 610.

The floss 102 may be placed under tension using the knob 118 to rotate the take-up assembly 116. The cap 130 may be used to provide a larger gripping surface and apply additional torque to the knob 118. Detents 740 on the shell 112 may be used to retain the cap 130 on the knob 118. The tension exerted by rotating the take-up assembly 116 may be used to advance the source floss 720 from the source spool 306 through the floss path described above when the button 122 is pressed. The tension may also be used to hold the floss suspended in a taught manner between the prong 104 and the guide 124 when the button 122 is released. The ratchet assembly 120 may bias the take-up assembly 116 against counter rotation to maintain tension on the floss 102 against the source spool 306.

If the floss breaks, pressing and holding the button 122 may release the source spool 306 and a length of floss 102 may be pulled out of the source chamber 318. The floss 102 may be then routed as described above, except that instead of threading the floss 102 through the take-up aperture 508, the broken end of the floss may be secured to the take-up assembly 116. The broken end of the floss 102 may be simply wrapped many times around the retie assembly 128 to secure it to the take-up assembly 116. In some embodiments, the broken end of the floss 102 is secured to the holding fin 622. A groove in the holding fin 622 may provide for a wrapping the floss around the holding fin, e.g., in a FIG. 8 pattern, similar to using a cleat. That is, the floss 102 may be wrapped around the retie assembly 128 on either side of the holding fin 622 in the retie assembly 128. The floss may be wrapped back and forth using the groove 628 to alternate the wrapping of the floss 102 between the two sides of the holding fin 622. Wrapping the floss 102 in an alternating path between either side of the holding fin 622 may secure the broken end of the floss 102 to the retie assembly 128.

The retie fin 624 may be disposed adjacent the take-up aperture 508, which in turn may be proximate the take-up spool 610. Once the slack in the floss 102 is taken up, further rotation of the take-up assembly 116 may tighten the floss 102 in the used floss groove 214 in the shaft 114 and the shell 112. The take-up assembly 116 may be further rotated until the retie groove 628 in the retie fin 624 is aligned with the take-up aperture 508.

When the floss is under tension and the retie groove 628 is aligned with the take-up aperture 508, the retie fin 624 may urge the floss 102 down through the take-up aperture 508 and into the take-up chamber 314 where the floss 102 may then be wrapped around the take-up spool 610. A portion of the secured floss 102 may be trapped between the aligned take-up aperture 508 and the retie fin as the take-up assembly 116 rotates the retie groove 628 past the take-up aperture 508. The angle between the trailing edge 626 and the radial may trap the floss 102 between the trailing edge 626 and the take-up aperture 508. Further rotation of the retie assembly 128 may result in the trailing edge 626 pushing the floss 102 down through the take-up aperture 508 and into the take-up chamber 314, thus, urging the trapped portion of the floss 102 into the take-up aperture 508 using the retie fin 624. That is, as the knob 118 continues to rotate the retie assembly 128, the take-up aperture 508 may cooperate with the retie groove 628 to bend the secured floss 102 around the retie fin 624 at the retie groove 628, and initiate wrapping the floss 102 around the take-up spool 610.

Once the broken end of the floss 102 begins wrapping around the take-up spool 610, multiple additional turns of the take-up assembly 116 may secure the plurality windings of the broken end of the floss 102 to the take-up spool 610. The retie groove 628 may further draw the floss 102 secured to the take-up spool 610 down into the take-up aperture 508 as the take-up assembly 116 continues to rotate, thus, wrapping the plurality of turns of the trapped floss 102 around the take-up spool 610. The broken floss is then retied, and the flosser 100 is ready for continued use. Optionally, after the floss 102 is secured to the take-up spool 610, the portion of the floss 102 wrapped around the retie assembly 128 may be cut off of the flosser 100.

In the course of developing the flosser 100, an unexpected problem was discovered that used floss would jam in the take-up chamber 314. As the take-up spool 610 winds up used floss, multiple layers of used floss 724 windings typically accumulate around the take-up spool 610 in a region adjacent the take-up aperture 508. The top layers of the accumulated windings of the used floss 724 eventually interfere with the inner surface of the shell 112. Further rotation of the take-up spool 610 jams the used floss 724 between the take-up spool 610 and the and the inner surface of the shell 112, thus stopping rotation of the take-up assembly 116.

Various experiments using a shell 112 having a smooth inner surface have demonstrated that this jamming effect. Increasing the smoothness of the inner surface of the shell 112 did little to prevent jamming. Adding grooves to the inner surface of the shell 112 increased jamming. Experiments with a helical grooves in the take-up spool 610 resulted in the used floss accumulating at an end of the take-up spool 610 opposite the take-up aperture 508 where it also jammed. Further experiments with a conical shaped shaft on the take-up spool 610 were unsuccessful. Similarly, experiments with a conical shaped shell on the take-up were also unsuccessful. Moreover, the tooling that would have been required to produce a conical shaped shell was determined to be prohibitively complicated and expensive. Grooves around the circumference of the inner surface of would require prohibitively complicated and expensive tooling, and would be expected to increase jamming. However, in the course of developing the flosser 100, an unexpected result was discovered that helical grooves around the inner surface of the shell 112 prevented jamming of the used floss 724. Moreover, it was also discovered that tooling for internal helical grooves is relatively inexpensive and uncomplicated.

The helical grooves 516 were discovered to prevent jamming that otherwise would have occurred as the diameter of the windings of used floss 724 around the take-up spool 610 begins to approach the inner diameter of the shell 112. The helical grooves 516 prevent the diameter of the windings of the used floss 724 from exceeding or even ataining the inner diameter of the shell 112, thus, jamming is avoided. As the diameter of the accumulating windings approaches the inner diameter of the shell 112, the helical grooves 516 urge the top layers of the windings of the used floss 724 forward (away from the take-up aperture 508) along the shaft of the take-up spool 610, to a region where the diameter of the windings of used floss 724 is substantially less than the inner diameter of the shell 112. This occurs as the take-up spool 610 rotates with respect the helical grooves 516. This prevents jamming of the floss between the take-up spool 610 and the shell 112.

Referring to FIGS. 1, 12, and 36, the cap 130 and may be used to cover a portion of the shaft 114 for protecting the prong 104, guide 124 and floss 102 from contamination. The cap 130 may also be removed from the shaft 114 and used to engage splines 126 on the knob 118, to provide an extension of the body 110 for griping and rotating the knob 118. The drain holes 134 may permit water to drain from the cap 130 after rinsing. An optional clip 132 may be attached to the cap 130 and serve to secure the flosser in a pocket.

Referring to FIG. 36, the shell 112 includes detent 740, stop 742, and detent 744. The detent 740 may engage the inner groove of the cap 130 to retain the cap 130 on the body 110 during flossing and while rotating the knob 118. The stop 742 may prevent the cap from interfering with the button 122. The detent 744 may engage the inner groove of the cap 130 to retain the cap 130 on the head of the body 110 to protect the prong 104, the guide 124, and floss 102 from dirt, contamination, and debris while the flosser 100 is not in use. The shell 112 further includes external splines 746 that may be aligned with the internal splines 136 of the cap 130 to provide stability and prevent rotation of the cap 130 with respect to the body 110.

The embodiments discussed herein are illustrative. As these embodiments are described with reference to illustrations, various modifications or adaptations of the methods and/or specific structures described may become apparent to persons of ordinary skill in the art. Various features and aspects of the above described technology may be used individually or jointly. Features in each of the various illustrations may be combined with features in other illustrations or used individually for illustrating the present technology. All such modifications, adaptations, or variations that rely upon the teachings of the embodiments, and through which these teachings have advanced the art, are considered to be within the spirit and scope of the present application. Hence, these descriptions and drawings should not be considered in a limiting sense, as it is understood that the present application is in no way limited to only the embodiments illustrated.

What is claimed is:

1. A retiable flosser comprising:
   a shaft including a head for supporting floss, the shaft further including spring forks;
   a source spool disposed on the shaft, the source spool for dispensing floss to the head;
   a take-up assembly disposed on the shaft, the take-up assembly including:
      a take-up spool for collecting used floss;
      a knob coupled to the take-up spool and configured to rotate the take-up spool for advancing used floss, the knob and spring forks forming a ratchet assembly for biasing direction of rotation of the take-up assembly, and
      a retie assembly disposed between the knob and the take-up spool and coupled to the take-up spool and knob, the retie assembly comprising:
         a first and second fin, and
         a retie groove disposed in the first and second fins, the retie groove configured for wrapping and securing an end of broken floss about the first fin; and
   a cylindrical shell for enclosing the source spool and the take-up spool, the shell including a take-up aperture adjacent the second fin and proximate the take-up spool, while the end of the floss is secured to the first fin, the second fin and retie groove being configured to urge a portion of the secured floss into the take-up aperture as the knob rotates the retie groove into alignment with the take-up aperture, and as the knob continues to rotate the retie assembly, the take-up aperture being further configured bend the portion of the secured floss around the second fin at the retie groove and wrap the floss around the take-up spool.

2. The flosser of claim 1, wherein the second fin includes an angle in the retie groove for trapping the floss between the second fin and the take-up groove.

3. The flosser of claim 1, wherein the shell includes helical grooves disposed in an inner surface of the shell.

4. The flosser of claim 1, wherein the groove in the first fin is aligned with the groove in the second fin.

5. The flosser of claim 1, further comprising:
- a prong disposed on the shaft for inserting floss between a tooth and a brace wire attached to the tooth;
- a guide disposed on the shaft for supporting the floss; and
- a button for releasing the source spool to release tension on the floss.

6. The flosser of claim 1, further comprising a seal between the source spool and the take-up spool.

7. The flosser of claim 1, further comprising a seal between the source spool and the take-up spool, the seal comprising
- a bearing disposed between the source spool and the take-up spool and configured to form an interference fit around a portion of the shaft;
- a chamber for collecting water from the source spool; and
- a drain hole for releasing the water.

8. A flosser comprising:
- a take-up spool for winding a plurality of layers of used floss;
- a shell for forming a chamber around the take-up spool and enclosing the plurality of layers of used floss windings around the take-up spool within the chamber; and
- helical grooves disposed in an inner surface of the shell, the helical grooves configured for urging a top layer of the floss windings along the take-up spool as the take-up spool rotates with respect to the shell, thereby preventing jamming of the take-up spool by the floss windings.

9. The flosser of claim 8, further comprising a knob coupled to the take-up spool and external to the shell, the knob configured for rotating the take-up spool.

10. The flosser of claim 8, further comprising:
- a knob coupled to the take-up spool and external to the shell, the knob including external splines and configured for rotating the take-up spool; and
- a cap including internal splines configured to align with the external splines of knob for applying torque to the knob.

11. The flosser of claim 8, further comprising:
- a take-up aperture disposed in the shell proximate the take-up spool;
- a knob external to the shell;
- a fin disposed between the knob and the take-up spool, the knob coupled to the fin and the take-up spool for rotating the fin and the take-up spool; and
- a groove disposed in the fin, the fin and groove configured for trapping the floss against the take-up aperture as the groove aligns with the take-up aperture, the fin configured for urging floss into take-up aperture as the knob rotates the fin; and the take-up aperture configured to admit floss for wrapping around the take-up spool as the knob further rotates the fin.

12. The flosser of claim 8, further comprising:
- a take-up aperture disposed in the shell proximate the take-up spool;
- a knob external to the shell;
- a fin disposed between the knob and the take-up spool, the knob coupled to the fin and the take-up spool for rotating the fin and the take-up spool; and
- a groove disposed in the fin, the fin and groove configured for trapping the floss against the take-up aperture as the groove aligns with the take-up aperture, and for urging floss into take-up aperture as the knob rotates the fin.

13. The flosser of claim 8, further comprising:
- a head for suspending floss, the head including
  - a prong for inserting floss between a tooth and a brace wire attached to the tooth, and
  - a guide for supporting the floss;
- a source spool for providing source floss to the head, the take-up spool further configured to apply tension to the floss; and
- a button for releasing the source spool to release tension on the floss.

* * * * *